United States Patent [19]
Jackson et al.

[11] Patent Number: 6,095,999
[45] Date of Patent: Aug. 1, 2000

[54] METHOD OF FORMING PETAL TIP TAMPON APPLICATORS

[75] Inventors: Dane R. Jackson, Bloomingdale; Christina M. Bremer, Edison, both of N.J.

[73] Assignee: Playtex Products, Inc., Westport, Conn.

[21] Appl. No.: 09/148,038

[22] Filed: Sep. 3, 1998

[51] Int. Cl.[7] .................................................. A61F 13/20
[52] U.S. Cl. ................................................. 604/14; 604/15
[58] Field of Search ........................... 604/904, 11–18, 604/285–288

[56] References Cited

U.S. PATENT DOCUMENTS

| | | | |
|---|---|---|---|
| 3,433,225 | 3/1969 | Voss et al. | 604/14 |
| 3,882,869 | 5/1975 | Hanke . | |
| 4,453,925 | 6/1984 | Decker | 604/14 |
| 4,543,086 | 9/1985 | Johnson . | |
| 5,279,541 | 1/1994 | Frayman et al. . | |
| 5,290,501 | 3/1994 | Klesius . | |
| 5,348,534 | 9/1994 | Tomaszewski et al. . | |
| 5,389,067 | 2/1995 | Rejai . | |
| 5,501,063 | 3/1996 | Tews et al. | 604/14 |
| 5,569,177 | 10/1996 | Fox et al. . | |
| 5,681,894 | 10/1997 | Williams et al. . | |
| 5,693,009 | 12/1997 | Fox et al. . | |
| 5,702,553 | 12/1997 | Iskra et al. . | |

*Primary Examiner*—John G. Weiss
*Assistant Examiner*—Dennis Ruhl
*Attorney, Agent, or Firm*—Ohlandt, Greeley, Ruggiero & Perle, L.L.P.

[57] ABSTRACT

A method of forming a cardboard tampon applicator having a petal tip is disclosed, in which a permanent plasticizer, preferably a hydrophilic plasticizer, is applied to at least a portion of the petal tip. Tampon applicators formed by this method are also disclosed.

21 Claims, 1 Drawing Sheet

METHOD OF FORMING PETAL TIP TAMPON APPLICATORS

BACKGROUND OF THE INVENTION

1. Field of the Invention

The present invention relates generally to a cardboard or other paper-based tampon applicator having petal tips at the insertion end. More particularly, the present invention relates to a method of softening the petals at the insertion end of a cardboard tampon applicator by means of a chemical softening agent, and the tampon applicators formed by that process. The tampon applicators having such softened petals are easier and more comfortable to insert than traditional petal-tip tampon applicators.

2. Description of Related Art

A variety of commercial tampon applicators available on the market are formed from cardboard or other paper-based materials, such as paperboard or paper laminate (collectively referred to herein as "cardboard"). However, cardboard tampon applicators formed of two telescoping tubes can be perceived by consumers as difficult and uncomfortable to insert. Petal-tip cardboard applicators have been developed to address this problem. Petals formed at the insertion end of the barrel of the tampon applicator are formed into a dome shape over the leading edge of the pledget. The resulting rounded shape is perceived as easier to insert than the blunt-end tampon applicators known in the art. The petals also protect the pledget.

One consequence of the use of such petal-tip applicators is the increased pressure necessary to open the petals to expel the pledget from the tampon applicator. Obviously, the user must press the plunger with sufficient pressure to force the pledget to open the petals and then pass through the petals. If too much pressure or force is needed, it can make the tampon applicator less acceptable to the consumer.

A variety of methods have been employed to address this issue. Most methods involve the partial perforation or weakening of the cardboard, either at the base of the petal, or at some portion of the petal nearer to the tip. However, this additional perforation or weakening process requires costly and exacting manufacturing steps. Moreover, the resulting tampon applicator is vulnerable to tearing or collapse at the site of the perforation or weakened region.

Coatings have been applied to the outside or exterior surface of the barrel of a tampon applicator. These coatings, which include cellophane, polyester and polyethylene coatings and films, can cover the petal tips of the barrel. Such coatings would typically strengthen and stiffen the petals, thus increasing the force needed to open the petals in order to expel the pledget.

Accordingly, an improved method of lowering the pressure to expel the pledget through the petal tip is needed.

BRIEF SUMMARY OF THE INVENTION

Accordingly, it is an object of the present invention to provide a method of softening the petal tips of a cardboard tampon applicator.

It is a further object of the present invention to provide a tampon applicator having chemically softened petal tips.

It is another object of the present invention to provide such a tampon applicator that is easy and comfortable to insert.

Accordingly, the present invention discloses a method of forming a cardboard tampon applicator having a petal tip, in which a permanent plasticizer, preferably a hydrophilic plasticizer, is applied to at least a portion of the petal tip. Tampon applicators formed by this method are also disclosed.

DETAILED DESCRIPTION OF THE INVENTION

Figure 1:
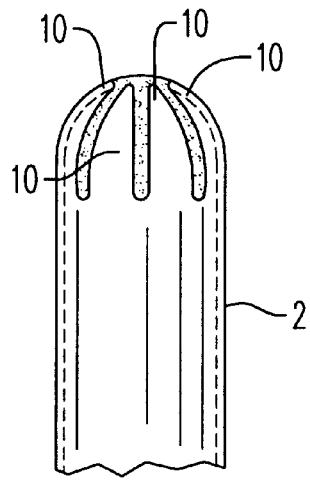
FIG. 1 illustrates the ejection end of a preferred embodiment of the present invention.
Figure 2:
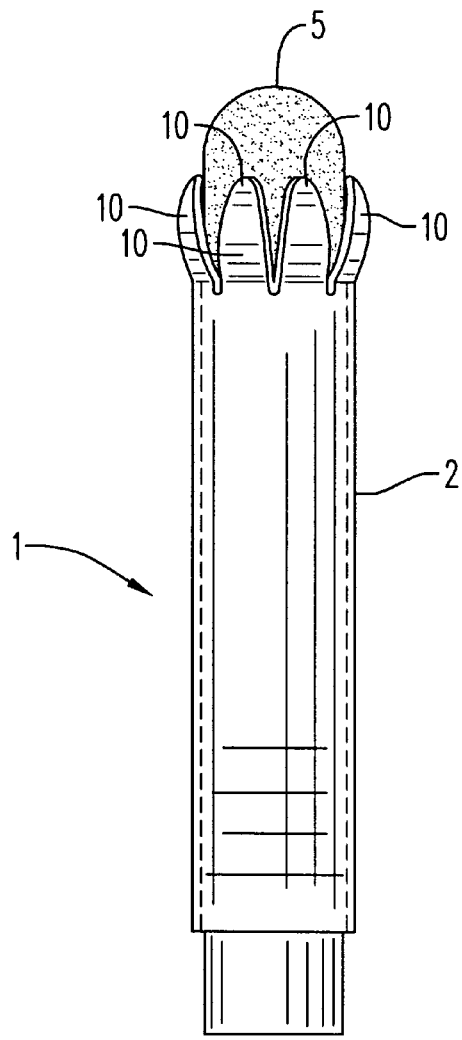
FIG. 2 illustrates the ejection end of FIG. 1, but with a partially ejected pledget.

The cardboard tampon applicators of the present invention, generally 1 have uniquely softened petal tips 10. A plasticizer is applied to some portion or all of the petal surfaces to effect this softening. The resulting petals are uniformly softer and more flexible than untreated petals, yet are able to maintain the desired shape during insertion but before expulsion of the pledget 5. The softened petals of the present invention allow the pledget to be expelled from the barrel with less force, generally illustrated in FIG. 2 thus making insertion easier and more comfortable, and increasing consumer confidence in the consistent performance of the tampon applicator.

The chemical softening agent or plasticizer that is applied to the petals is a permanent plasticizer that will not readily evaporate when exposed to air or moisture. The addition of a plasticizer to the petal region results in a permanent reduction in petal stiffness. The plasticizer works by lubricating the fibers of the cardboard so that they are able to slide and flex over each other more easily.

The permanent plasticizer is preferably a hydrophilic plasticizer. A hydrophilic plasticizer interrupts the stiff hydrogen bonds between the cellulose molecules of the cardboard. In effect, the plasticizer increases the flexibility of the cardboard. Such a plasticizer is easy to apply, and produces a pliable but firm petal tip that is ideally suited for use in a cardboard tampon applicator.

It has been found that preferred hydrophilic plasticizers for use include glycerin, polysorbate 20, and an organosilicone, such as a dimethicone copolyol (e.g., dimethyl, methyl(polyethylene oxide) siloxane), either individually or in combination, or in combination with water. Of the foregoing, the plasticizer most preferably includes an organosilicone. Of the organosilicones preferred for use as plasticizers herein, most preferred is a polysiloxy linoleyl pyrrolidone phospholipid. This organosilicone is commercially available as Monasil PLN from Mona Industries, Inc. It has increased polarity, thus rendering it mild and water soluble. It has a pH of about 6.5, and a specific gravity at 25° C. of 1.00, and is highly substantive.

The plasticizer is preferably applied to the petal region at a minimum level of about 5 mg per barrel, generally 2, to effect a permanent reduction in stiffness. Levels greater than about 20 mg per barrel have been found to negatively effect the stability of the petal curvature, and are consequently less preferred. Consequently, plasticizer is preferably applied at about 5 mg to about 20 mg per barrel, or more preferably at about 10 mg to about 18 mg per barrel. More specifically, when polysiloxy linoleyl pyrrolidone phospholipid is used as the plasticizer, it is preferably applied at about 16 mg per barrel.

The plasticizer is preferably diluted in the water used to spray the inner surface of the petals before final petal formation (see U.S. Pat. No. 5,290,501, discussed below). The preferred dilution level is dependent upon the amount of water being sprayed and the desired amount of plasticizer to be applied. Most preferably, the plasticizer is diluted to about 10% to about 25% by weight in water for ease of application.

The following table, Table 1, demonstrates the reduction in petal stiffness, as measured by petal flex, when treated with two different levels of a preferred plasticizer of the present invention. Petal flex is the force in grams required to open a single petal to the point that the petal tip is in line with the barrel's inner surface.

TABLE 1

| Solution | Amount* (mg) | Petal Flex | | | Stat. Sign.** |
| --- | --- | --- | --- | --- | --- |
| | | AVG | STD | N | |
| Water (control) | 0 | 63.6 | 9.1 | 20 | — |
| 10% Dimethicone copolyol | 6 | 53.9 | 10.2 | 20 | Yes |
| 10% Polysorbate 20 | 6 | 44.0 | 10.4 | 20 | Yes |
| 10% Glycerin | 6 | 47.7 | 7.1 | 20 | Yes |
| 25% Dimethicone copolyol | 15 | 47.9 | 6.6 | 20 | Yes |
| 25% Polysorbate 20 | 15 | 49.7 | 5.4 | 20 | Yes |
| 25% Glycerin | 15 | 49.0 | 11.0 | 20 | Yes |

*Amount of permanent hydrophilic plasticizer applied
**Statistically significant (≧99% confidence level) difference as compared to the control A separate test of polysiloxy linoleyl pyrrolidone phospholipid demonstrates its effectiveness as a petal plasticizer, as summarized in Table 2.

TABLE 2

| Solution | Amount* (mg) | Ejection Force (oz) | STD | N = | Petal Flex (g) | STD | N = |
| --- | --- | --- | --- | --- | --- | --- | --- |
| Water (control) | 0 | 16.07 | 2.5 | 50 | 51.78 | 7.9 | 30 |
| 20% polysiloxy linoleyl pyrrolidone phospholipid | 16 | 13.24 | 1.4 | 50 | 44.94 | 6.5 | 30 |

*calculated amount of chemical plasticizer applied

These data show the treated petals to have a significant reduction (99% confidence level—statistical method: non-paired student t test) of 18% over the control petals in ejection force and of 13% over the control petals in petal flex.

The petal forming temperature and time for the super-sized test barrel is about 265° F. to about 315° F. for about seven seconds. The petals are traditionally plasticized temporarily by an application from about 50 mg to about 80 mg of water, which then evaporates as the petals form in the heated dome. In the test examples of Table 2, in order to best simulate manufacturing conditions, a plastic pump bottle was used that delivered an average spray of about 80 mg, which translates to about 16 mg potential add-on of polysiloxy linoleyl pyrrolidone phospholipid (neat). The interior of the petals on polyethylene terephthalate-coated barrels were sprayed with either 1) a 20% solution of polysiloxy linoleyl pyrrolidone phospholipid, or 2) distilled water (control), and then were formed on a post-former at about 265° F. to about 315° F. from about 7 to about 10 seconds. The petals were then left to stabilize overnight.

For both test and control, fifty barrels were assembled with conventional pledgets and coated plungers to evaluate ejection force by the Instron method. Also, fifteen unassembled barrels were tested by the Instron method for petal flex; two petals on opposite sides (not on the seam) were tested on each barrel, yielding thirty data points for each sample.

A method of chemically softening or plasticizing the petals of a cardboard tampon applicator is also provided herein. It is preferred that only the petal region of the tampon applicator is treated. It is believed that treatment of the non-petal areas would raise the cost. Also, such treatment would unnecessarily lower the tampon applicator's resistance to being radially crushed. Preferably, the inner face of each petal is treated with the plasticizer. However, both the inner and outer faces of each petal can be treated with the plasticizer. Moreover, only a proportion of the petals, or only a portion of the surface of each petal, can be treated.

According to a preferred method of forming a petal-tip tampon applicator of the present invention, the applicators are formed by die cutting a petal-tip form in a flat blank and then forming a tube. Alternatively, petal tips can be die cut into a previously formed applicator tube. Both preferred methods result in a tampon applicator with the petals curved in the circumferential direction only. A subsequent radial inward curving step is required to complete the formation (i.e., the "closing") of the petals. This further curving of the petals has been found to work best when the cardboard is moist.

The moisture applied to the petals and/or the tube acts as a transitory softener (it evaporates and/or migrates away from the petals) and results in better petal formation. This moisture may come from the moisture left over from laminating the paper plies together or may be externally applied, preferably as is disclosed in U.S. Pat. No. 5,290,501, the disclosure of which is incorporated herein. Because the moisture is a transitory softener, it has no permanent plasticizing effect. Thus, the cardboard reverts to its intrinsic stiffness.

While conventional petal tips include a plurality of (typically six) approximately triangular shaped petals that curve to form a substantially complete dome shape, it should be understood that the present invention is not limited to the shape of the petals. Petals of other shapes may be used. The petals need not meet fully; part of the pledget surface may remain exposed. The petals may overlap, and they need not form a domed shape.

Various modifications may be made as will be apparent to those skilled in the art. Thus, it will be obvious to one of ordinary skill in the art that the foregoing description and drawings are merely illustrative of certain preferred embodiments of the present invention, and that various obvious modifications can be made to these embodiments in accordance with the spirit and scope of the appended claims.

What is claimed is:

1. A method of forming a cardboard tampon applicator barrel having a petal tip, comprising applying a permanent plasticizer to at least a portion of said petal tip.

2. The method of claim 1, wherein said plasticizer is hydrophilic.

3. The method of claim 2, wherein said plasticizer is selected from the group consisting of glycerin, an organosilicone, polysorbate 20, and combinations thereof.

4. The method of claim 3, wherein said plasticizer includes polysiloxy linoleyl pyrrolidone phospholipid.

5. The method of claim 1, wherein said plasticizer is diluted in water before application to said petal tip.

6. The method of claim 5, wherein said plasticizer is diluted from about 10% to about 25% by weight in water.

7. The method of claim 1, wherein said plasticizer is applied to an inner surface of said petal tip.

8. The method of claim 1, wherein said plasticizer is sprayed on said petal tip.

9. The method of claim 1, wherein said plasticizer is only applied to said petal tip of said tampon applicator.

10. The method of claim 1, wherein said plasticizer is applied in an amount from about 5 mg to about 20 mg to said barrel.

11. The method of claim 1, wherein said plasticizer is applied in an amount from about 10 mg to about 18 mg to said barrel.

12. The method of claim 1, further comprising the step of heating said tampon applicator with said permanent plasticizer at about 265° F. to about 315° F.

13. The method of claim 12, wherein said heating step lasts from about 7 seconds to about 10 seconds.

14. The tampon applicator formed by the method of claim 1, said tampon applicator comprising a coating of plasticizer on said at least a portion of said petal tip.

15. A tampon applicator comprising:
   a plunger; and
   a barrel having a rear end adapted to receive said plunger; said barrel having a front end with a petal tip, said petal tip being coated with a permanent plasticizer that softens said petal tip.

16. The tampon applicator of claim 15, wherein said permanent plasticizer is a hydrophilic plasticizer.

17. The tampon applicator of claim 16, wherein said hydrophilic plasticizer is selected from the group consisting of glycerin, polysorbate 20, an organosilicone and combinations thereof.

18. The tampon applicator of claim 17, wherein said hydrophilic plasticizer includes polysiloxy linoleyl pyrrolidone phospholipid.

19. The tampon applicator of claim 15, wherein said plasticizer is diluted in water before application to said petal tip.

20. The tampon applicator of claim 19, wherein said plasticizer is diluted from about 10% to about 25% by weight in water.

21. The tampon applicator of claim 15, wherein said plasticizer is applied to an inner surface of said petal tip.

* * * * *